US009642818B2

(12) United States Patent
Giordano et al.

(10) Patent No.: US 9,642,818 B2
(45) Date of Patent: *May 9, 2017

(54) COMPOSITIONS AND METHODS FOR NUTRITION SUPPLEMENTATION

(71) Applicant: Exeltis USA, Inc., Chatham, NJ (US)

(72) Inventors: John A Giordano, West Orange, NJ (US); Charles J. Balzer, Lavalette, NJ (US)

(73) Assignee: Exeltis USA, Inc., Chatham, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/182,745

(22) Filed: Feb. 18, 2014

(65) Prior Publication Data

US 2014/0161907 A1  Jun. 12, 2014

Related U.S. Application Data

(63) Continuation of application No. 13/489,510, filed on Jun. 6, 2012, now abandoned, which is a continuation of application No. 11/928,610, filed on Oct. 30, 2007, now Pat. No. 8,197,855, which is a continuation of application No. 10/916,534, filed on Aug. 12, 2004, now Pat. No. 7,560,123.

(51) Int. Cl.

| | | |
|---|---|---|
| *A61K 8/67* | (2006.01) |
| *A61K 31/07* | (2006.01) |
| *A61K 9/00* | (2006.01) |
| *A61K 31/015* | (2006.01) |
| *A61K 31/355* | (2006.01) |
| *A61K 31/375* | (2006.01) |
| *A61K 31/4415* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 31/593* | (2006.01) |
| *A61K 31/714* | (2006.01) |
| *A61K 33/06* | (2006.01) |
| *A61K 33/08* | (2006.01) |
| *A61K 33/26* | (2006.01) |
| *A61K 33/30* | (2006.01) |
| *A61K 45/06* | (2006.01) |
| *A61K 31/4406* | (2006.01) |
| *A61K 31/715* | (2006.01) |

(52) U.S. Cl.
CPC ............ *A61K 31/07* (2013.01); *A61K 9/0056* (2013.01); *A61K 31/015* (2013.01); *A61K 31/355* (2013.01); *A61K 31/375* (2013.01); *A61K 31/4406* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/593* (2013.01); *A61K 31/714* (2013.01); *A61K 31/715* (2013.01); *A61K 33/06* (2013.01); *A61K 33/08* (2013.01); *A61K 33/26* (2013.01); *A61K 33/30* (2013.01); *A61K 45/06* (2013.01); *Y10S 514/904* (2013.01)

(58) Field of Classification Search
None
See application file for complete search history.

(56) References Cited

U.S. PATENT DOCUMENTS

| | | | | |
|---|---|---|---|---|
| 6,495,177 | B1 * | 12/2002 | deVries et al. ................ | 426/72 |
| 7,560,123 | B2 * | 7/2009 | Giordano ............... | A61K 33/30 |
| | | | | 424/614 |
| 8,101,587 | B2 * | 1/2012 | Giordano .............. | A23L 1/3008 |
| | | | | 514/168 |
| 8,197,855 | B2 * | 6/2012 | Giordano ............... | A61K 33/30 |
| | | | | 424/641 |
| 8,609,629 | B2 * | 12/2013 | Giordano .............. | A23L 1/3008 |
| | | | | 514/168 |
| 9,271,519 | B2 * | 3/2016 | Giordano .............. | A23L 1/3008 |
| 2004/0197430 | A1 * | 10/2004 | Meyrowitz ................... | 424/756 |
| 2005/0054682 | A1 * | 3/2005 | Phillips ......................... | 514/338 |
| 2006/0188607 | A1 * | 8/2006 | Schramm et al. .............. | 426/72 |

OTHER PUBLICATIONS

Vitafol PN (NDC 0642-0078) Apr. 12, 2002.*
Ladipo, Am J Clin Nutr Jul. 2000 vol. 72 No. 1 280-290.*
Complaint for Patent Infringement and Jury Demand, *Everett Laboratories, Inc.* v. *Acella Pharmaceuticals, LLC*, Case No. 1:13-cv-03487-KM-MCA, Dkt No. 1 (U.S. Dist. Ct. Dist. of N.J. Filed Jun. 5, 2013).
Notice of Motion for Preliminary Injunction and Exhibits 1-30 with Declaration of Robert Schoenberg, *Everett Laboratories, Inc.* v. *Acella Pharmaceuticals, LLC*, Case No. 1:13-cv-03487-KM-MCA, Dkt. No. 8 (U.S. Dist. Ct. Dist. of N.J. Filed Jul. 1, 2013).
Acella's Answer and Counterclaim, *Everett Laboratories, Inc.* v. *Acella Pharmaceuticals, LLC*, Case No. 1:13-cv-03487-KM-MCA, Dkt. No. 22 (U.S. Dist. Ct. Dist. of N.J. Filed Jul. 24, 2013).
Acella's Opposition to Motion for Preliminary Injunction and Exhibits 1-13, *Everett Laboratories, Inc.* v. *Acella Pharmaceuticals, LLC*, Case No. 1:13-cv-03487-KM-MCA, Dkt. No. 38 (U.S. Dist. Ct. Dist. of N.J. Filed Aug. 8, 2013).

(Continued)

*Primary Examiner* — Robert A Wax
*Assistant Examiner* — Melissa Mercier
(74) *Attorney, Agent, or Firm* — Don J. Pelto; Sheppard Mullin Richter & Hampton LLP

(57) ABSTRACT

The present invention relates to compositions that may be swallowable, chewable or dissolvable, comprising various vitamins and minerals, and in a specific embodiment comprising vitamin A, beta carotene, B-complex vitamins, vitamin C, vitamin D$_3$, vitamin E, iron, magnesium and zinc, and methods for using these compositions for nutritional supplementation in subjects undergoing physiologically stressful events, such as, for example and without limitation, pregnancy, lactation or any disease state.

34 Claims, No Drawings

(56) References Cited

OTHER PUBLICATIONS

Declaration of J. Schramm with Exhibits A-D, *Everett Laboratories, Inc.* v. *Acella Pharmaceuticals, LLC*, Case No. 1:13-cv-03487-KM-MCA, Dkt No. 39 (U.S. Dist. Ct. Dist. of N.J. Filed Aug. 8, 2013).
Reply Brief by Everett Labs with Attachments 1-23, *Everett Laboratories, Inc.* v. *Acella Pharmaceuticals, LLC*, Case No. 1:13-cv-03487-KM-MCA, Dkt. No. 53 (U.S. Dist. Ct. Dist. of N.J. Filed Aug. 16, 2013).
Opinion, *Everett Laboratories, Inc.* v. *Acella Pharmaceuticals, LLC*, Case No. 1:13-cv-03487-KM-MCA, Dkt. No. 65 (U.S. Dist. Ct. Dist. of N.J. Filed Aug. 29, 2013).
Order denying Preliminary Injunction, *Everett Laboratories, Inc.* v. *Acella Pharmaceuticals, LLC*, Case No. 1:13-cv-03487-KM-MCA, Dkt. No. 66 (U.S. Dist. Ct. Dist. of N.J. Filed Aug. 29, 2013).
Answer to Counterclaim, *Everett Laboratories, Inc.* v. *Acella Pharmaceuticals, LLC*, Case No. 1:13-cv-03487-KM-MCA, Dkt. No. 67 (U.S. Dist. Ct. Dist. of N.J. Filed Sep. 3, 2013).
Amended Opinion, *Everett Laboratories, Inc.* v. *Acella Pharmaceuticals, LLC*, Case No. 1:13-cv-03487-KM-MCA, Dkt. No. 69 (U.S. Dist. Ct. Dist. of N.J. Filed Sep. 13, 2013).
Motion to Amend/Correct Invalidity and Noninfringement Contentions, *Everett Laboratories, Inc.* v. *Acella Pharmaceuticals, LLC*, Case No. 1:13-cv-03487-KM-MCA, Dkt. No. 86 (U.S. Dist. Ct. Dist. of N.J. Filed Nov. 6, 2013).
Order granting Motion to Amend/Correct, *Everett Laboratories, Inc.* v. *Acella Pharmaceuticals, LLC*, Case No. 1:13-cv-03487-KM-MCA, Dkt. No. 94 (U.S. Dist. Ct. Dist. of N.J. Filed Dec. 3, 2013).
Letter from Robert Schoenberg with Joint Claim Construction and Prehearing Statement, *Everett Laboratories, Inc.* v. *Acella Pharmaceuticals, LLC*, Case No. 1:13-cv-03487-KM-MCA, Dkt. No. 101 (U.S. Dist. Ct. Dist. of N.J. Filed Jan. 10, 2014).
Order regarding discovery confidentiality order, *Everett Laboratories, Inc.* v. *Acella Pharmaceuticals, LLC*, Case No. 1:13-cv-03487-KM-MCA, Dkt. No. 104 (U.S. Dist. Ct. Dist. of N.J. Filed Jan. 21, 2014).
Letter from Christopher Kinkade with Amended Joint Claim Construction and Prehearing Statement, *Everett Laboratories, Inc.* v. *Acella Pharmaceuticals, LLC*, Case No. 1:13-cv-03487-KM-MCA, Dkt. No. 106 (U.S. Dist. Ct. Dist. of N.J. Filed Jan. 21, 2014).
Letter from Robert Schoenberg with Markman Brief and Exhibits (Attachments 1-16), *Everett Laboratories, Inc.* v. *Acella Pharmaceuticals, LLC*, Case No. 1:13-cv-03487-KM-MCA, Dkt. No. 107 (U.S. Dist. Ct. Dist. of N.J. Filed Jan. 21, 2014).
Acella's Opening Markman Brief with Attachments 1-7, *Everett Laboratories, Inc.* v. *Acella Pharmaceuticals, LLC*, Case No. 1:13-cv-03487-KM-MCA, Dkt. No. 108 (U.S. Dist. Ct. Dist. of N.J. Filed Jan. 21, 2014).
Everett's Markman Response Brief, *Everett Laboratories, Inc.* v. *Acella Pharmaceuticals, LLC*, Case No. 1:13-cv-03487-KM-MCA, Dkt. No. 122 (U.S. Dist. Ct. Dist. of N.J. Filed Feb. 11, 2014).
Acella's Markman Response Brief, *Everett Laboratories, Inc.* v. *Acella Pharmaceuticals, LLC*, Case No. 1:13-cv-03487-KM-MCA, Dkt. No. 123 (U.S. Dist. Ct. Dist. of N.J. Filed Feb. 11, 2014).
Signed Consent Judgment and Permanent Injunction, *Everett Laboratories, Inc.* v. *Acella Pharmaceuticals, LLC*, Case No. 1:13-cv-03487-KM-MCA, Dkt. No. 134 (U.S. Dist. Ct. Dist. of N.J. Filed Apr. 2, 2014).
Complaint, *Everett Laboratories, Inc.* v. *Acella Pharmaceuticals, LLC*, Case No. 1:13-cv-07603-JEI-KMW, Dkt. No. 1 (U.S. Dist. Ct. Dist. of N.J. Filed Dec. 17, 2013).
Answer and Counterclaim, *Everett Laboratories, Inc.* v. *Acella Pharmaceuticals, LLC*, Case No. 1:13-cv-07603-JEI-KMW, Dkt. No. 10 (U.S. Dist. Ct. Dist. of N.J. Filed Jan. 22, 2014).
Answer to Counterclaim, *Everett Laboratories, Inc.* v. *Acella Pharmaceuticals, LLC*, Case No. 1:13-cv-07603-JEI-KMW, Dkt. No. 22 (U.S. Dist. Ct. Dist. of N.J. Filed Feb. 17, 2014).
Letter with Proposed Consent Judgment and Permanent Injunction, *Everett Laboratories, Inc.* v. *Acella Pharmaceuticals, LLC*, Case No. 1:13-cv-07603-JEI-KMW, Dkt. No. 29 (U.S. Dist. Ct. Dist. of N.J. Filed Mar. 27, 2014).
Signed Consent Judgment and Permanent Injunction, *Everett Laboratories, Inc.* v. *Acella Pharmaceuticals, LLC*, Case No. 1:13-cv-07603-JEI-KMW, Dkt. No. 30 (U.S. Dist. Ct. Dist. of N.J. Filed Apr. 2, 2014).

\* cited by examiner

COMPOSITIONS AND METHODS FOR NUTRITION SUPPLEMENTATION

CROSS REFERENCE TO RELATED APPLICATION

This application is a continuation and claims the benefit, under 35 U.S.C. §120, of U.S. patent application Ser. No. 13/489,510, filed Jun. 6, 2012, now abandoned, which is a continuation of U.S. patent application Ser. No. 11/928,610, filed Oct. 30, 2007, issued as U.S. Pat. No. 8,197,855 on Jun. 12, 2012, which is a continuation of U.S. patent application Ser. No. 10/916,534, filed Aug. 12, 2004, issued as U.S. Pat. No. 7,560,123 on Jul. 14, 2009. The entire contents and substance of these applications are hereby incorporated by reference.

FIELD OF THE INVENTION

The present invention relates to compositions, that may be swallowable, chewable and/or dissolvable, comprising various vitamins and minerals, and methods for using these compositions for nutritional supplementation in, for example, subjects in physiologically stressful states.

BACKGROUND OF THE INVENTION

Nutrition plays a critical role in maintaining good health. Proper nutrition prevents dietary deficiencies, and also protects against the development of disease. When the body faces physiological stress, proper nutrition plays an increasingly important role. For example, pregnancy and lactation are among the most nutritionally volatile and physiologically stressful periods and processes in the lifetimes of women. Vitamin and mineral needs are almost universally increased during these natural processes. Increased vitamin and mineral needs during these times are almost always due to elevated metabolic demand, increased plasma volume, increased levels of blood cells, decreased concentrations of nutrients, and decreased concentrations of nutrient-binding proteins.

When increased nutrient needs occur during pregnancy, lactation, or any other physiologically stressful state, nutritional supplementation serves a vital role in maintaining good health. Nutritional supplementation is especially pertinent to women contemplating conceiving a child because optimizing specific nutrients before, during, and after the physiological processes of pregnancy or lactation can have profound, positive, and comprehensive impacts upon the overall wellness of the developing and newborn child as well as on the safety and health of the mother. The present invention provides compositions and methods designed to supplement the nutritional needs of individuals in physiologically stressful states.

Further, while some patients may prefer swallowable dosage forms, it is estimated that 50% of the population has problems swallowing whole tablets. Seager, 50 J. PHARM. PHARMACOL. 375-82 (1998). These problems can lead to poor, or even noncompliance, with dosing regimens and thus have negative impacts on treatment efficiency. Id. Administration of vitamins and minerals through chewable or dissolvable compositions solves this problem because the compositions need not be swallowed whole.

SUMMARY OF THE INVENTION

The present invention provides compositions and methods of using these compositions for both prophylactic and therapeutic nutritional supplementation. Specifically, for example, the present invention relates to novel compositions of vitamins and minerals that can be used to supplement the nutritional deficiencies observed in patients undergoing physiologically stressful states such as, for example and without limitation, pregnancy, lactation, and any disease state. The compositions of the present invention may be in a swallowable, chewable or dissolvable form according to an individual patient's preference. Choice in dosage form promotes ease of administration and compliance with dosing regimens.

In one embodiment of the present invention, the compositions may comprise vitamin A, beta carotene, B-complex vitamins, vitamin C, vitamin $D_3$, vitamin E, iron, magnesium, and zinc.

In another embodiment, the compositions of the present invention may comprise one or more of vitamin A in the form of acetate; beta carotene; vitamin $B_1$ in the form of thiamine mononitrate; vitamin $B_2$ in the form of riboflavin; vitamin $B_3$ in the form of niacinamide or niacin; vitamin $B_6$ in the form of pyridoxine hydrochloride; vitamin $B_9$ in the form of folic acid, folacin, metafolin, folate and/or one or more natural isomers of folate including (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof and 5-formimino-(6S)-tetrahydrofolic acid or a polyglutamyl derivative thereof; vitamin $B_{12}$ in the form of cyanocobalamin; vitamin C in the form of ascorbic acid; vitamin $D_3$ in the form of cholecalciferol; vitamin E in the form of d-alpha tocopheryl acetate or d-alpha tocopheryl succinate; iron in the form of polysaccharide complex or ferrous fumarate; magnesium in the form of magnesium oxide; and/or zinc in the form of zinc oxide.

In another embodiment of the present invention, the compositions may be substantially free of any other added vitamins and minerals not described in the preceding paragraph. For example, the compositions of the present invention may be substantially free of added alpha carotene; substantially free of added lutein; substantially free of added lycopene; substantially free of added zeaxanthin; substantially free of added vitamin $B_4$; substantially free of added vitamin $B_5$; substantially free of added vitamin $B_7$; substantially free of added vitamin $B_8$; substantially free of added vitamin $B_{10}$; substantially free of added vitamin $B_{11}$; substantially free of added calcium; substantially free of added chromium; substantially free of added copper; substantially free of added manganese; substantially free of added selenium; substantially free of added boron; substantially free of added odorless garlic; substantially free of added coenzyme Q-10; substantially free of added 1-carnitine; substantially free of added grape seed extract; substantially free of added green tea extract; substantially free of added quercetin; substantially free of added hawthorne berries; and/or substantially free of added alpha lipoic acid.

In another specific embodiment, the compositions of the present invention may be substantially free of added vitamin A; substantially free of added beta carotene; substantially free of added vitamin $B_1$; substantially free of added vitamin $B_2$; substantially free of added vitamin $B_3$; substantially free of added vitamin $B_6$; substantially free of added vitamin $B_9$; substantially free of added vitamin $B_{12}$; substantially free of added vitamin C; substantially free of added vitamin $D_3$;

substantially free of added vitamin E; substantially free of added iron; substantially free of added magnesium; and/or substantially free of added zinc.

In another embodiment, the compositions of the present invention may comprise pharmaceutically acceptable carriers, such as one or more of binders, diluents, lubricants, glidants, colorants, emulsifiers, disintegrants, starches, water, oils, alcohols, preservatives, and sugars.

In another embodiment of the present invention, the compositions may comprise sweetening agents such as one or more of sucrose, fructose, high fructose corn syrup, dextrose, saccharin sodium, maltodextrin, aspartame, potassium acesulfame, neohesperidin dihydrochalcone, sucralose, monoammonium glycyrrhizinate, and mixtures thereof.

In another embodiment of the present invention, the compositions may comprise flavorants such as one or more of anise oil, cinnamon oil, peppermint oil, oil of wintergreen, clove oil, bay oil, anise oil, eucalyptus oil, thyme oil, cedar leave oil, oil of nutmeg, oil of sage, oil of bitter almonds, cassia oil, lemon oil, orange oil, lime oil, grapefruit oil, grape oil, apple essence, pear essence, peach essence, berry essence, wildberry essence, date essence, blueberry essence, kiwi essence, strawberry essence, raspberry essence, cherry essence, plum essence, pineapple essence, apricot essence, natural mixed berry flavor, citric acid, malic acid, vanilla, vanillin, cocoa, chocolate, and menthol.

In another embodiment of the present invention, the compositions may comprise an alkyl polysiloxane in the form of dimethyl polysiloxane.

In another embodiment, the compositions of the present invention may comprise one or more of about 550 IU to about 1650 IU vitamin A; about 300 IU to about 900 IU beta carotene; about 1 mg to about 3 mg vitamin $B_1$; about 1 mg to about 3 mg vitamin $B_2$; about 7 mg to about 23 mg vitamin $B_3$; about 1 mg to about 4 mg vitamin $B_6$; about 500 µg to about 1500 µg vitamin $B_9$; about 2 µg to about 8 µg vitamin $B_{12}$; about 30 mg to about 90 mg vitamin C; about 200 IU to about 600 IU vitamin $D_3$; about 15 IU to about 45 IU vitamin E; about 14 mg to about 44 mg iron; about 12 mg to about 38 mg magnesium; and about 7 mg to about 23 mg zinc.

In another embodiment, the compositions of the present invention may comprise one or more of about 880 IU to about 1320 IU vitamin A; about 480 IU to about 720 IU beta carotene; about 1.3 mg to about 1.9 mg vitamin $B_1$; about 1.5 mg to about 2.2 mg vitamin $B_2$; about 12 mg to about 18 mg vitamin $B_3$; about 2 mg to about 3 mg vitamin $B_6$; about 800 µg to about 1200 µg vitamin $B_9$; about 4 µg to about 6 µg vitamin $B_{12}$; about 48 mg to about 72 mg vitamin C; about 320 IU to about 480 IU vitamin $D_3$; about 24 IU to about 36 IU vitamin E; about 23 mg to about 35 mg iron; about 20 mg to about 30 mg magnesium; and about 12 mg to about 18 mg zinc.

In another embodiment of the present invention, the compositions may comprise one or more of about 990 IU to about 1210 IU vitamin A; about 540 IU to about 660 IU beta carotene; about 1.5 mg to about 1.75 mg vitamin $B_1$; about 1.6 mg to about 2 mg vitamin $B_2$; about 13.5 mg to about 16.5 mg vitamin $B_3$; about 2.3 mg to about 2.8 mg vitamin $B_6$; about 900 µg to about 1100 µg vitamin $B_9$; about 4.5 µg to about 5.5 µg vitamin $B_{12}$; about 54 mg to about 66 mg vitamin C; about 360 IU to about 440 IU vitamin $D_3$; about 27 IU to about 33 IU vitamin E; about 26 mg to about 32 mg iron; about 22.5 mg to about 27.5 mg magnesium; and about 13.5 mg to about 16.5 mg zinc.

In another embodiment of the present invention, the compositions may comprise one or more of about 1100 IU vitamin A; about 600 IU beta carotene; about 1.6 mg vitamin $B_1$; about 1.8 mg vitamin $B_2$; about 15 mg vitamin $B_3$; about 2.5 mg vitamin $B_6$; about 1000 µg vitamin $B_9$; about 5 µg vitamin $B_{12}$; about 60 mg vitamin C; about 400 IU vitamin $D_3$; about 30 IU vitamin E; about 29 mg iron; about 25 mg magnesium; and about 15 mg zinc.

In another embodiment of the present invention, the compositions may be suitable for administration to subjects in physiologically stressful states, such as those resulting from pregnancy, lactation or disease states. Such compositions may be suitable for treating nutritional deficiencies resulting from such physiologically stressful states, which may result from, for example and without limitation, elevated metabolic demand, increased plasma volume, or decreased concentrations of nutrient-binding proteins such as, for example and without limitation, serum-ferritin, maltose-binding protein, lactoferrin, calmodulin, tocopheryl binding protein, riboflavin binding protein, retinol binding protein, transthyretin, high density lipoprotein-apolipoprotein A1, folic acid binding protein and 25-hydroxyvitamin D binding protein.

The present invention also includes methods of administering the compositions of the invention to patients to supplement nutritional deficiencies resulting from, for example and without limitation, pregnancy, lactation, and any disease state.

In one embodiment of the present invention, the methods may utilize compositions comprising vitamin A, beta carotene, B-complex vitamins, vitamin C, vitamin $D_3$, vitamin E, iron, magnesium and zinc. In another embodiment of the present invention, the methods may utilize compositions in a swallowable, chewable, or dissolvable form.

In another embodiment of the present invention, the methods may utilize compositions including vitamin A in the form of acetate; beta carotene; vitamin $B_1$ in the form of thiamine mononitrate; vitamin $B_2$ in the form of riboflavin; vitamin $B_3$ in the form of niacinamide or niacin; vitamin $B_6$ in the form of pyridoxine hydrochloride; vitamin $B_9$ in the form of folic acid, folacin, metafolin, folate and/or one or more natural isomers of folate including (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof and 5-formimino-(6S)-tetrahydrofolic acid or a polyglutamyl derivative thereof; vitamin $B_{12}$ in the form of cyanocobalamin; vitamin C in the form of ascorbic acid; vitamin $D_3$ in the form of cholecalciferol; vitamin E in the form of d-alpha tocopheryl acetate or d-alpha tocopheryl succinate; iron in the form of polysaccharide complex or ferrous fumarate; magnesium in the form of magnesium oxide; and zinc in the form of zinc oxide.

In another embodiment of the present invention, the methods may utilize compositions substantially free of any other added vitamins and minerals not described in the preceding paragraph. For example, the methods may utilize compositions that are substantially free of added alpha carotene; substantially free of added lutein; substantially free of added lycopene; substantially free of added zeaxanthin; substantially free of added vitamin $B_4$; substantially free of added vitamin $B_5$; substantially free of added vitamin $B_7$; substantially free of added vitamin $B_8$; substantially free of added vitamin $B_{10}$; substantially free of added vitamin $B_{11}$; substantially free of added calcium; substantially free of added chromium; substantially free of added copper; substantially free of added manganese; substantially free of added selenium; substantially free of added boron; substantially free of added odorless garlic; substantially free of added coenzyme Q-10; substantially free of added 1-carnitine; substantially free of added grape seed extract; substantially free of added green tea extract; substantially free of added quercetin; substantially free of added hawthorne berries; and/or substantially free of added alpha lipoic acid.

In another specific embodiment, the methods may utilize compositions that are substantially free of added vitamin A; substantially free of added beta carotene; substantially free of added vitamin $B_1$; substantially free of added vitamin $B_2$; substantially free of added vitamin $B_3$; substantially free of added vitamin $B_6$; substantially free of added vitamin $B_9$; substantially free of added vitamin $B_{12}$; substantially free of added vitamin C; substantially free of added vitamin $D_3$; substantially free of added vitamin E; substantially free of added iron; substantially free of added magnesium; and/or substantially free of added zinc.

In another embodiment of the present invention, the methods may utilize compositions comprising pharmaceutically acceptable carriers, such as one or more of binders, diluents, lubricants, glidants, colorants, emulsifiers, disintegrants, starches, water, oils, alcohols, preservatives, and sugars.

In another embodiment of the present invention, the methods may utilize compositions comprising sweetening agents such as one or more of sucrose, fructose, high fructose corn syrup, dextrose, saccharin sodium, maltodextrin, aspartame, potassium acesulfame, neohesperidin dihydrochalcone, sucralose, monoammonium glycyrrhizinate, and mixtures thereof.

In another embodiment of the present invention, the methods may utilize compositions comprising flavorants such as one or more of anise oil, cinnamon oil, peppermint oil, oil of wintergreen, clove oil, bay oil, anise oil, eucalyptus oil, thyme oil, cedar leave oil, oil of nutmeg, oil of sage, oil of bitter almonds, cassia oil, lemon oil, orange oil, lime oil, grapefruit oil, grape oil, apple essence, pear essence, peach essence, berry essence, wildberry essence, date essence, blueberry essence, kiwi essence, strawberry essence, raspberry essence, cherry essence, plum essence, pineapple essence, apricot essence, natural mixed berry flavor, citric acid, malic acid, vanilla, vanillin, cocoa, chocolate, and menthol.

In another embodiment of the present invention, the methods may utilize compositions comprising an alkyl polysiloxane in the form of dimethyl polysiloxane.

In another embodiment, the methods may utilize compositions comprising one or more of about 550 IU to about 1650 IU vitamin A; about 300 IU to about 900 IU beta carotene; about 1 mg to about 3 mg vitamin $B_1$; about 1 mg to about 3 mg vitamin $B_2$; about 7 mg to about 23 mg vitamin $B_3$; about 1 mg to about 4 mg vitamin $B_6$; about 500 µg to about 1500 µg vitamin $B_9$; about 2 µg to about 8 µg vitamin $B_{12}$; about 30 mg to about 90 mg vitamin C; about 200 IU to about 600 IU vitamin $D_3$; about 15 IU to about 45 IU vitamin E; about 14 mg to about 44 mg iron; about 12 mg to about 38 mg magnesium; and about 7 mg to about 23 mg zinc.

In another embodiment of the present invention, the methods may utilize compositions comprising one or more of about 880 IU to about 1320 IU vitamin A; about 480 IU to about 720 IU beta carotene; about 1.3 mg to about 1.9 mg vitamin $B_1$; about 1.5 mg to about 2.2 mg vitamin $B_2$; about 12 mg to about 18 mg vitamin $B_3$; about 2 mg to about 3 mg vitamin $B_6$; about 800 µg to about 1200 µg vitamin $B_9$; about 4 µg to about 6 µg vitamin $B_{12}$; about 48 mg to about 72 mg vitamin C; about 320 IU to about 480 IU vitamin $D_3$; about 24 IU to about 36 IU vitamin E; about 23 mg to about 35 mg iron; about 20 mg to about 30 mg magnesium; and about 12 mg to about 18 mg zinc.

In another embodiment of the present invention, the methods may utilize compositions comprising one or more of about 990 IU to about 1210 IU vitamin A; about 540 IU to about 660 IU beta carotene; about 1.5 mg to about 1.75 mg vitamin $B_1$; about 1.6 mg to about 2 mg vitamin $B_2$; about 13.5 mg to about 16.5 mg vitamin $B_3$; about 2.3 mg to about 2.8 mg vitamin $B_6$; about 900 µg to about 1100 µg vitamin $B_9$; about 4.5 µg to about 5.5 µg vitamin $B_{12}$; about 54 mg to about 66 mg vitamin C; about 360 IU to about 440 IU vitamin $D_3$; about 27 IU to about 33 IU vitamin E; about 26 mg to about 32 mg iron; about 22.5 mg to about 27.5 mg magnesium; and about 13.5 mg to about 16.5 mg zinc.

In another embodiment of the present invention, the methods may utilize compositions comprising one or more of about 1100 IU vitamin A; about 600 IU beta carotene; about 1.6 mg vitamin $B_1$; about 1.8 mg vitamin $B_2$; about 15 mg vitamin $B_3$; about 2.5 mg vitamin $B_6$; about 1000 µg vitamin $B_9$; about 5 µg vitamin $B_{12}$; about 60 mg vitamin C; about 400 IU vitamin $D_3$; about 30 IU vitamin E; about 29 mg iron; about 25 mg magnesium; and about 15 mg zinc.

In another embodiment of the present invention, the methods may utilize compositions suitable for administration to subjects in physiologically stressful states, such as those resulting from, for example and without limitation, pregnancy, lactation or disease states. Such compositions may be suitable for treating nutritional deficiencies resulting from such physiologically stressful states, which may result from, for example and without limitation, elevated metabolic demand, increased plasma volume, or decreased concentrations of nutrient-binding proteins such as serum-ferritin, maltose-binding protein, lactoferrin, calmodulin, tocopheryl binding protein, riboflavin binding protein, retinol binding protein, transthyretin, high density lipoprotein-apolipoprotein A1, folic acid binding protein and 25-hydroxyvitamin D binding protein.

Other objectives, features and advantages of the present invention will become apparent from the following detailed description. The detailed description and the specific examples, although indicating specific embodiments of the invention, are provided by way of illustration only. Accordingly, the present invention also includes those various changes and modifications within the spirit and scope of the invention that may become apparent to those skilled in the art from this detailed description.

DETAILED DESCRIPTION OF THE INVENTION

It is understood that the present invention is not limited to the particular methodologies, protocols, fillers, excipients, etc...., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a vitamin" is a reference to one or more vitamins and includes equivalents thereof known to those skilled in the art and so forth.

Unless defined otherwise, all technical and scientific terms used herein have the same meanings as commonly understood by one of ordinary skill in the art to which this invention belongs. Specific methods, devices, and materials are described, although any methods and materials similar or equivalent to those described herein can be used in the practice or testing of the present invention.

The term "disease state" as used herein, may comprise any state in which one or more organs or components of an organism malfunction. The term "disease state" may refer to any deterioration of any component of a body. The term "disease state" may refer to any deficiency of any compound necessary for the maintenance or function of any component of any organism. The term "disease state" may refer to any condition in which a body contains toxins, produced by microorganisms that infect the body or by body cells through faulty metabolism or absorbed from an external source. "Disease states" may be adverse states caused by any diet, any virus, or any bacteria. "Disease states" may comprise disorders associated with pregnant females such as, for example, osteomalacia and preeclampsia and disorders associated with a fetus such as, for example, neural tube defects and various fetal abnormalities. "Disease states" may comprise any pulmonary disorder such as, for example, bronchitis, bronchiectasis, atelectasis, pneunomia, diseases caused by inorganic dusts, diseases caused by organic dusts, any pulmonary fibrosis and pleurisy. "Disease states" may comprise any hematological/oncological disorder such as, for example, anemia, hemophilia, leukemia, and lymphoma. A "disease state" may comprise any cancer such as, for example and without limitation, breast cancer, lung cancer, prostate cancer, pancreatic cancer, liver cancer, stomach cancer, testicular cancer, ovarian cancer, skin cancer, cancer of the brain, cancer of the mouth, cancer of the throat, and cancer of the neck. "Disease states" may comprise any disorder of the immune system such as, for example, acquired immune deficiency syndrome (AIDS), AIDS-related complex, infection by any strain of any human immunodeficiency virus (HIV), and other viruses or pathogens such as bacteria. A "disease state" may comprise any cardiovascular disorder such as, for example, arterial hypertension, orthostatic hypotension, arteriosclerosis, coronary artery disease, cardiomyopathy, any arrhythmia, any valvular heart disease, endocarditis, pericardial disease, any cardiac tumor, any aneurysm and any peripheral vascular disorder. "Disease states" may comprise any hepatic/biliary disorder such as, for example and without limitation, jaundice, hepatic steatosis, fibrosis, cirrhosis, hepatitis, any hepatic granuloma, any liver tumor, cholelithiasis, cholecystitis and choledocholithiasis.

The term "physiologically stressful state," as used herein, comprises any state of an organism in which the organism faces one or more physiological challenges. A "physiologically stressful state" may comprise, for example and without limitation, pregnancy, lactation, or conditions in which an organism faces physiological challenges related to, for example and without limitation, elevated metabolic demand, increased plasma volume, or decreased concentrations of nutrient-binding proteins. A "physiologically stressful state" may result from one or more disease states.

The term "subject," as used herein, comprises any and all organisms and includes the term "patient." "Subject" may refer to a human or any other animal. "Subject" also may refer to a fetus.

The phrase "pharmaceutically acceptable," as used herein, refers to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "swallowable form" refers to any compositions that do not readily dissolve when placed in the mouth and may be swallowed whole without any chewing or discomfort. Such compositions, in one embodiment, may have a shape containing no sharp edges and a smooth, uniform and substantially bubble free outer coating.

The phrase "chewable form" refers to any relatively soft compositions that are chewed in the mouth after oral administration, have a pleasant taste and mouthfeel, and quickly break into smaller pieces and begin to dissolve after chewing such that they can be swallowed substantially as a solution.

The phrase "dissolvable form" refers to any compositions that dissolve into a solution in the mouth. Such compositions, in one embodiment, may dissolve within about 60 seconds or less after placement in the mouth without any chewing.

The term "mouthfeel" refers to non-taste-related aspects of the pleasantness experienced by a person while chewing or swallowing a nutritional supplement. Aspects of mouthfeel include, for example and without limitation, the hardness and brittleness of a composition, whether the composition is chewy, gritty, oily, creamy, watery, sticky, easily dissolved, astringent, effervescent, and the like, and the size, shape, and form of the composition (tablet, powder, gel, etc. . . . ).

The term "antioxidant" means an agent which inhibits oxidation and thus is used to prevent deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and others known to those of ordinary skill in the art.

Proper nutrition is essential for maintaining health and preventing diseases. Adequate nutrition is especially critical during, for example, nutritionally volatile or physiologically stressful periods such as those including, by way of example and without limitation, pregnancy, lactation, or any disease state. Vitamin and mineral needs are almost universally increased throughout these periods. Increased needs during physiologically stressful states such as pregnancy, lactation or disease state may result from elevated metabolic demand, increased plasma volume, increased quantities of circulating red blood cells, decreased concentrations of nutrients, and decreased concentrations of nutrient-binding proteins such as, for example and without limitation, serum-ferritin, maltose-binding protein, lactoferrin, calmodulin, tocopheryl binding protein, riboflavin binding protein, retinol binding protein, transthyretin, high density lipoprotein-apolipoprotein A1, folic acid binding protein, and 25-hydroxyvitamin D binding protein. Lapido, 72 (Supp.) AMER. J. CLIN. NUTR. 280S-90S (2000).

Optimizing specific nutrients before, during, and after the physiological processes of pregnancy and lactation can have profound, positive, and comprehensive impacts on the overall wellness of the developing and newborn child as well as on the safety and health of the mother. Black, 85 (Supp.) BRIT. J. NUTR. S193-97 (2001); Scholl et al., 146 AMER. J. EPIDEM. 134-41 (1997). Nutrients provided to a mother reach the fetus. Specifically, it is established that substrates for growth and development, for example, circulate within the same pathways that carry drugs to and waste products from the fetus. Exchanges of material between mother and fetus occur primarily in the placenta, where villi containing fetal capillaries protrude into sinuses (intervillous spaces). Maternal arterial blood spurts into these spaces, then drains into maternal uterine veins to be returned to the maternal systemic circulation. Solutes in maternal blood cross the epithelial cells and connective tissue of the villi and the endothelium of the fetal capillaries; these solutes are then carried to the fetus by placental veins, which converge into the umbilical vein. THE MERCK MANUAL OF DIAGNOSIS AND THERAPY 2022 (Mark H. Beers, M.D. & Robert Berkow, M.D., eds., 17th ed. 1999).

The compositions and methods of the present invention provide the means to optimize good health by utilizing vitamin and mineral nutritional supplementation. The compositions and methods of the present invention may be administered to or directed to a subject such as a human or any other organism.

The compositions and methods of the present invention may include vitamin A. Vitamin A is involved in physiological processes that result in cellular differentiation, cellular maturity, and cellular specificity. Thus, vitamin A is an important component of a nutritional supplement for subjects in physiologically stressful states, such as those caused by pregnancy, lactation or disease state. Zile et al., 131(3) J. NUTR. 705-08 (2001). In a specific embodiment of the present invention, vitamin A may be included in the form of acetate. In another specific embodiment, vitamin A may be included in amounts ranging from about 550 IU to about 1650 IU. In another specific embodiment, vitamin A may be included in amounts ranging from about 880 IU to about 1320 IU. In another specific embodiment, vitamin A may be included in amounts ranging from about 990 IU to about 1210 IU. In another embodiment, vitamin A may be included in an amount of about 1100 IU.

The compositions and methods of the present invention may include beta carotene. Beta carotene is converted to vitamin A within the body as needed. Mayne, 10 J. FASEB 690-701 (1996). Beta carotene also has powerful antioxidant properties. Antioxidants are important during physiologically stressful events for numerous reasons. For example, lipid peroxidation has been associated with over 200 disease processes. Rock et al., 96(7) J. AMER. DIET. ASSOC. 693-702 (1996). Antioxidants are especially important during pregnancy because in the first trimester, establishment of blood flow into the intervillous space is associated with a burst of oxidative stress. The inability to mount an effective antioxidant defense against this burst results in early pregnancy loss. Myatt & Cui, HISTOCHEM. CELL BIOL., DOI: 10.1007/s00418-004-0677-x (Jul. 10, 2004). Further, oxidative stress has been implicated in the pathophysiology of preeclampsia, a toxemia of pregnancy. Llurba et al., 37(4) FREE RADIC. BIOL. MED. 557-70 (2004). Finally, oxidative stress during pregnancy plays an important role in fetal growth, and healthy antioxidant levels are positively correlated with birth weight and length. Lee et al., EUR. J. CLIN. NUTR., DOI: 10.1038/sj.ejcn.160 (Mar. 31, 2004). In a specific embodiment of the present invention, beta carotene may be included in amounts ranging from about 300 IU to 900 IU. In another specific embodiment of the present invention, beta carotene may be included in amounts ranging from about 480 IU to 720 IU. In another specific embodiment of the present invention, beta carotene may be included in amounts ranging from about 540 IU to 660 IU. In another embodiment, beta carotene may be included in an amount of about 600 IU.

The compositions and methods of the present invention may comprise or use B-complex vitamins. This class of vitamins comprises water-soluble nutrients generally not stored in the body. They play roles in a variety of biological processes critical to the health of pregnant women, lactating women, and fetuses such as, for example, the metabolism of homocysteine. The B-complex vitamins that may be included in the compositions and methods of the present invention comprise one or more of vitamin $B_1$, vitamin $B_2$, vitamin $B_3$, vitamin $B_6$, vitamin $B_9$ and vitamin $B_{12}$.

The compositions and methods of the present invention may comprise or use vitamin $B_1$. Vitamin $B_1$ plays a role in carbohydrate metabolism and neural function. It is a coenzyme for the oxidative decarboxylation of alpha-ketoacids (e.g., alpha-ketoglutarate and pyruvate) and for transketolase, which is a component of the pentose phosphate pathway. NATIONAL RESEARCH COUNCIL, RECOMMENDED DIETARY ALLOWANCES 123 (10th ed. 1989) (hereinafter "RDA"). In a specific embodiment of the present invention, vitamin $B_1$ may be included in the form of thiamine mononitrate. In another specific embodiment, vitamin $B_1$ may be included in amounts ranging from about 1 mg to about 3 mg. In another specific embodiment, vitamin $B_1$ may be included in amounts ranging from about 1.3 mg to about 1.9 mg. In another specific embodiment, vitamin $B_1$ may be included in amounts ranging from about 1.5 mg to about 1.75 mg. In another embodiment, vitamin $B_1$ may be included in an amount of about 1.6 mg.

The compositions and methods of the present invention may comprise or use vitamin $B_2$. Vitamin $B_2$ is a component of two flavin coenzymes, flavin mononucleotide (FMN) and flavin adenine dinucleotide (FAD). These flavoenzymes are involved in a number of oxidation-reduction reactions including the conversion of pyridoxine and niacin. RDA, supra at 132. Flavoenzymes also play a role in a number of metabolic pathways such as amino acid deamination, purine degradation and fatty acid oxidation and thus help to maintain carbohydrate, amino acid and lipid metabolism. In a specific embodiment of the present invention, vitamin $B_2$ may be included in the form of riboflavin. In another specific embodiment, vitamin $B_2$ may be included in amounts ranging from about 1 mg to about 3 mg. In another specific embodiment, vitamin $B_2$ may be included in amounts ranging from about 1.5 mg to about 2.2 mg. In another specific embodiment, vitamin $B_2$ may be included in amounts ranging from about 1.6 mg to about 2 mg. In another embodiment, vitamin $B_2$ may be included in an amount of about 1.8 mg.

The compositions and methods of the present invention may comprise or use vitamin $B_3$. Vitamin $B_3$, or "niacin" is the common name for two compounds: nicotinic acid (also called niacin) and niacinamide (also called nicotinamide). Vitamin $B_3$ is particularly important for maintaining healthy levels and types of fatty acids. It is also required for the synthesis of pyroxidine, riboflavin, and folic acid. RDA, supra at 137. Administration of vitamin $B_3$ also may effect a reduction in total cholesterol (LDL) and very low density lipoprotein (VLDL) levels and an increase in high density lipoprotein (HDL) cholesterol levels. Nicotinamide adenine dinucleotide (NAD) and NAD phosphate (NADP) are active coenzymes of niacin. These coenzymes are involved in numerous enzymatic reactions such as glycolysis, fatty acid metabolism, and steroid synthesis. Henkin et al., 91 AM. J. MED. 239-46 (1991). In a specific embodiment of the present invention, vitamin $B_3$ may be included in the form of niacinamide. In another specific embodiment, the present invention may include an equivalent molar amount of niacin. In another specific embodiment, vitamin $B_3$ may be included in amounts ranging from about 7 mg to about 23 mg. In another specific embodiment, vitamin $B_3$ may be included in amounts ranging from about 12 mg to about 18 mg. In another specific embodiment, vitamin $B_3$ may be included in amounts ranging from about 13.5 mg to about 16.5 mg. In another embodiment, vitamin $B_3$ may be included in an amount of about 15 mg.

The compositions and methods of the present invention may comprise or use vitamin $B_6$. The administration of vitamin $B_6$ may reduce the levels of homocysteine. Bostom et al., 49 KIDNEY INT. 147-52 (1996). The active forms of vitamin $B_6$, pyridoxal-5'-phosphate (PLP) and pyridoxamine-5'-phosphate, are coenzymes for numerous enzymes and as such, are important for gluconeogenesis, niacin formation, and erythrocyte metabolism. RDA, supra at 142-43. Vitamin $B_6$ is a coenzyme for both cystathionine synthase and cystathionase, enzymes that catalyze the formation of cysteine from methionine. Homocysteine is an intermediate in this process and elevated levels of plasma homocysteine are recognized as a risk factor for both vascular disease (Robinson et al., 94 CIRCULATION 2743-48 (1996)) and neural tube defects (Locksmith & Duff, 91 OBSTET. GYNECOL. 1027-34 (1998)). In a specific embodiment of the present invention, vitamin $B_6$ may be included in the form of pyridoxine hydrochloride. In another specific embodiment, vitamin $B_6$ may be included in amounts ranging from about 1 mg to about 4 mg. In another specific embodiment, vitamin $B_6$ may be included in amounts ranging from about 2 mg to about 3 mg. In another specific embodiment, vitamin $B_6$ may be included in amounts ranging from about 2.3 mg to about 2.8 mg. In another embodiment, vitamin $B_6$ may be included in an amount of about 2.5 mg.

The compositions and methods of the present invention may comprise or use vitamin $B_9$. This vitamin has demonstrated the ability to prevent neural tube defects such as spina bifida caused by disturbed homocysteine metabolism. Vanderput et al., EXP. BIOL. MED. 243-70 (2001); DeFalco et al., 27 CLIN. EXP. OBSTET. GYNECOL. 188-90 (2000); Eskes, 27 CLIN. EXP. OBSTET. GYNECOL. 157-67 (2000); Locksmith & Duff, supra. Vitamin $B_9$ also is important for the formation of red and white blood cells within bone marrow and plays a role in heme formation. Further, folate deficiencies inhibit the activity of vitamin $B_1$. RDA, supra at 150. In a specific embodiment of the present invention, vitamin $B_9$ may be included in the form of folic acid. In another embodiment, vitamin $B_9$ may be included in the forms of folic acid, folacin, metafolin, folate and/or one or more natural isomers of folate including (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof and 5-formimino-(6S)-tetrahydrofolic acid or a polyglutamyl derivative thereof. In another specific embodiment, vitamin $B_9$ may be included in amounts ranging from about 500 μg to about 1500 μg. In another specific embodiment, vitamin $B_9$ may be included in amounts ranging from about 800 μg to about 1200 μg. In another specific embodiment, vitamin $B_9$ may be included in amounts ranging from about 900 μg to about 1100 μg. In another embodiment, vitamin $B_9$ may be included in an amount of about 1000 μg.

The compositions and methods of the present invention may comprise or use vitamin $B_{12}$. Vitamin $B_{12}$ can be converted to the active coenzymes, methylcobalamin and 5'-deoxyadenosylcobalamin. These coenzymes are necessary for folic acid metabolism, conversion of coenzyme A and myelin synthesis. Methylcobalamin also catalyzes the demthylation of a folate cofactor which is involved in DNA synthesis. A lack of demethylation may result in folic acid deficiency. RDA, supra at 159-160. Deoxyadenosylcobalamin is the coenzyme for the conversion of methylmalonyl-CoA to succinyl-CoA, which plays a role in the citric acid cycle. Cobalamin, along with pyridoxine and folic acid, also are implicated in the proper metabolism of homocysteine, a breakdown product of the amino acid methionine, which is correlated with an increased risk of heart disease due to its negative effects on endothelial function. In one specific embodiment of the present invention, vitamin $B_{12}$ may be included in the form of cyanocobalamin. In another specific embodiment, vitamin $B_{12}$ may be included in amounts ranging from about 2 μg to about 8 μg. In another specific embodiment, vitamin $B_{12}$ may be included in amounts ranging from about 4 μg to about 6 μg. In another specific embodiment, vitamin $B_{12}$ may be included in amounts ranging from about 4.5 μg to about 5.5 μg. In another embodiment, vitamin $B_{12}$ may be included in an amount of about 5 μg.

The compositions and methods of the present invention may comprise or use vitamin C. The major biochemical role of water-soluble vitamin C is as a co-substrate in metal catalyzed hydroxylations. Like beta carotene, vitamin C has antioxidant properties. It interacts directly with superoxide hydroxyl radicals and singlet oxygen, and also provides antioxidant protection for folate and vitamin E, keeping vitamin E in its most potent form. Vitamin C may afford protective effects against preeclampsia by participating in the scavenging of free radicals. Indeed, significantly lower levels of vitamin C have been observed in preeclamptic women than in controls. Woods et al., 185(1) AM. J. OBSTET. GYNECOL. 5-10 (2001); Kharb, 1 EURO. J. OBSTET. GYNECOL. REPRO. BIOL. 37-39 (2000); Milczarek et al., 210 MOL. CELL. BIOCHEM. 65-73 (2000).

Vitamin C also enhances the absorption of iron. RDA, supra at 115. In addition, vitamin C is required for collagen synthesis, epinephrine synthesis, and bile acid formation. Moreover, vitamin C has been implicated in inhibiting atherosclerosis by being present in extracellular fluid of the arterial wall and potentiating nitric oxide activity, thus normalizing vascular function. In a specific embodiment of the present invention, vitamin C may be included in the form of ascorbic acid. In another specific embodiment, vitamin C may be included in amounts ranging from about 30 mg to about 90 mg. In another specific embodiment, vitamin C may be included in amounts ranging from about 48 mg to about 72 mg. In another specific embodiment, vitamin C may be included in amounts ranging from about 54 mg to about 66 mg. In another embodiment, vitamin C may be included in an amount of about 60 mg.

The compositions and methods of the present invention may comprise or use vitamin $D_3$. Vitamin $D_3$ is a fat-soluble "hormone like" substance important for the maintenance of healthy bones. This vitamin increases the absorption of calcium and phosphorous from the gastrointestinal tract, and improves mineral resorption into bone tissue. Vitamin D can be converted to its active form from exposure of the skin to sunlight. This fact is among the reasons why vitamin D deficiency is common in the elderly, notably the institutionalized, who spend little or no time out of doors. Deficiencies in vitamin $D_3$ can lead to increased bone turnover and loss, and when severe, osteomalacia, or softening of the bones.

Supplementation with vitamin $D_3$ has been shown to moderately reduce bone loss, increase serum 25-hydroxyvitamin D, and decrease serum parathyroid hormone levels. Dawson-Hughes et al., 337 NEW ENG. J. MED. 670-76 (1997); Lips et al., 86 J. CLIN. ENDOCRINOL. METAB. 1212-21 (2001). Vitamin $D_3$ also plays a role in the maintenance of calcium and phosphorus homeostasis, but it is also active in cell differentiation and immune function. In a specific embodiment of the present invention, vitamin $D_3$ may be included in the form of cholecalciferol. In another specific embodiment, vitamin $D_3$ may be included in amounts ranging from about 200 IU to about 600 IU. In another specific embodiment, vitamin $D_3$ may be included in amounts ranging from about 320 IU to about 480 IU. In another specific embodiment, vitamin $D_3$ may be included in amounts ranging from about 360 IU to about 440 IU. In another embodiment, vitamin $D_3$ may be included in an amount of about 400 IU.

The compositions and methods of the present invention may comprise or use vitamin E. Vitamin E is a fat-soluble vitamin antioxidant found in biological membranes where it protects the phospholipid membrane from oxidative stress. Vitamin E inhibits the oxidation of unsaturated fatty acids by trapping peroxyl free radicals. It is also an antiatherogenic agent, and studies have demonstrated a reduced risk of coronary heart disease with increased intake of vitamin E. Stampfer et al., 328 NEW ENG. J. MED. 1444-49 (1993). In addition, vitamin E, like beta carotene and vitamin C, may afford protective effects against preeclampsia by participating in the scavenging of free radicals. As with vitamin C, significantly lower levels of vitamin E have been observed in preeclamptic women than in controls. Woods et al., supra; Kharb, supra; Milczarek et al., supra. In a specific embodiment of the present invention, vitamin E may be included in the form of d-alpha-tocopheryl acetate. In another specific embodiment, vitamin E may be included in the form of an equivalent molar amount of d-alpha tocopheryl succinate. In another specific embodiment, vitamin E may be included in amounts ranging from about 15 IU to about 45 IU. In another specific embodiment, vitamin E may be included in amounts ranging from about 24 IU to about 36 IU. In another specific embodiment, vitamin E may be included in amounts ranging from about 27 IU to about 33 IU. In another embodiment, vitamin E may be included in an amount of about 30 IU.

The compositions and methods of the present invention may comprise or use iron. A primary function of iron is to carry oxygen to bodily tissues via the hemoglobin part of red blood cells. Supplemental intake of iron is critical to preventing anemia, a disorder associated with a variety of physiological states including, for example, pregnancy. Bothwell, 72(Supp.) AM. J. CLIN. NUTR. 257S-64S (2000). Severe anemia may have adverse effects upon a mother and a fetus. Specifically, significant depression of hemoglobin has been associated with poor pregnancy outcome. Black, supra; Sifakis & Pharmakides, 900 ANN. N.Y. ACAD. SCI. 125-36 (2000). The compositions and methods of the present invention may include iron in either chelated or nonchelated form. In a specific embodiment of the present invention, iron may be included in the form of polysaccharide iron complex. In another specific embodiment, iron may be included in the form of an equivalent molar amount of ferrous fumarate. In another specific embodiment, iron may be included in amounts ranging from about 14 mg to about 44 mg. In another specific embodiment, iron may be included in amounts ranging from about 23 mg to about 35 mg. In another specific embodiment, iron may be included in amounts ranging from about 26 mg to about 32 mg. In another embodiment, iron may be included in an amount of about 29 mg.

The compositions and methods of the present invention may comprise or use magnesium. Magnesium is found primarily in both bone and muscle and is important for over 300 different enzyme reactions. A primary function of magnesium is to bind to phosphate groups in adenosine triphosphate (ATP), thereby forming a complex that assists in the transfer of ATP phosphate. Magnesium also functions within cells as a membrane stabilizer. Magnesium plays roles in nucleic acid synthesis, glycolysis, transcription of DNA and RNA, amino acid activation, membrane transport, transketolase reactions, and protein synthesis. James L. L. Groff et al., ADVANCED NUTRITION AND HUMAN METABOLISM 341 (2d ed. 1996). It is also involved in the formation of cAMP, a cytosolic second messenger that plays a role in cell signaling mechanisms. Magnesium also functions both synergistically and antagonistically with calcium in neuromuscular transmission. RDA, supra at 188. Specifically, magnesium is critical for the maintenance of electrochemical potentials of nerve and muscle membranes and the neuromuscular junction transmissions, particularly important in the heart. Not surprisingly, magnesium deficiency is tied to cardiovascular disease and hypertension. Agus et al., 17 CRIT. CARE CLIN. 175-87 (2001). Indeed, oral magnesium therapy improves endothelial function in patients with coronary disease. Shechter et al., 102 CIRCULATION 2353-58 (2000).

Magnesium is available in a variety of salts and can be included in the compositions and methods of the present invention in either chelated or nonchelated form. In one specific embodiment of the present invention, magnesium may be included in the form of magnesium oxide. In another specific embodiment, magnesium may be included in amounts ranging from about 12 mg to about 38 mg. In another specific embodiment, magnesium may be included in amounts ranging from about 20 mg to about 30 mg. In another specific embodiment, magnesium may be included in amounts ranging from about 22.5 mg to about 27.5 mg. In another embodiment, magnesium may be included in an amount of about 25 mg.

The compositions and methods of the present invention may comprise or use zinc. Zinc plays a role in numerous metabolic activities such as nucleic acid production, protein synthesis, and development of the immune system. There are more than 200 zinc metalloenzymes including aldolase, alcohol dehydrogenase, RNA polymerase, and protein kinase C. Zima et al., 17 BLOOD PURIF. 182-86 (1999). Zinc stabilizes RNA and DNA structures, forms zinc fingers in nuclear receptors, and is a component of chromatin proteins involved in transcription and replication. Deficiencies of zinc during pregnancy have been shown to contribute to severe fetal abnormalities. Srinivas et al., 68(6) INDIAN J. PEDIATR. 519-22 (2001); Yang et al., 13(4) BIOMED. ENVIRON. SCI. 280-86 (2000); King, 71(Supp.) AM. J. CLIN. NUTR. 1334S-43S (2000). Zinc is available in many forms and may be included in the compositions and methods of the present invention in chelated or nonchelated form. In a specific embodiment of the present invention, zinc may be included in the form of zinc oxide. In another specific embodiment, zinc may be included in amounts ranging from about 7 mg to about 23 mg. In another specific embodiment, zinc may be included in amounts ranging from about 12 mg to about 18 mg. In another specific embodiment, zinc may be included in amounts ranging from about 13.5 mg to about 16.5 mg. In another embodiment, zinc may be included in an amount of about 15 mg.

The compositions and methods of the present invention may comprise or use a combination of the included vitamins and minerals just described, in either chelated or nonchelated form. The active ingredients are available from numerous commercial sources, and in several active forms or salts thereof, known to those of ordinary skill in the art. Hence, the compositions and methods of the present invention are not limited to comprising or using any particular form of the vitamin or mineral ingredient described herein.

In a specific embodiment of the present invention, specific vitamins and/or minerals may be excluded. For example, in a specific embodiment, the compositions and methods of the present invention may be substantially free of added vitamin A; substantially free of added beta carotene; substantially free of added alpha carotene; substantially free of added lutein; substantially free of added lycopene; substantially free of added zeaxanthin; substantially free of added vitamin $B_1$; substantially free of added vitamin $B_2$; substantially free of added vitamin $B_3$; substantially free of added vitamin $B_4$; substantially free of added vitamin $B_5$; substantially free of added vitamin $B_6$; substantially free of added vitamin $B_7$; substantially free of added vitamin $B_8$; substantially free of added vitamin $B_9$; substantially free of added vitamin $B_{10}$; substantially free of added vitamin $B_{11}$; substantially free of added vitamin $B_{12}$; substantially free of added vitamin C; substantially free of added vitamin $D_3$; substantially free of added vitamin E; substantially free of added calcium; substantially free of added chromium; substantially free of added copper; substantially free of added magnesium; substantially free of added manganese; substantially free of added selenium; substantially free of added zinc; substantially free of added boron; substantially free of added odorless garlic; substantially free of added coenzyme Q-10; substantially free of added 1-carnitine; substantially free of added grape seed extract; substantially free of added green tea extract; substantially free of added quercetin; substantially free of added hawthorne berries; and/or substantially free of added alpha lipoic acid. In another embodiment of the present invention, the compositions are substantially free of other added vitamins and minerals.

A specific embodiment of the present invention may comprise swallowable compositions. Swallowable compositions are well known in the art and are those that do not readily dissolve when placed in the mouth and may be swallowed whole without any chewing or discomfort. In a specific embodiment of the present invention the swallowable compositions may have a shape containing no sharp edges and a smooth, uniform and substantially bubble free outer coating.

To prepare the swallowable compositions of the present invention, each of the active ingredients may be combined in intimate admixture with a suitable carrier according to conventional compounding techniques. In a specific embodiment of the swallowable compositions of the present invention, the surface of the compositions may be coated with a polymeric film. Such a film coating has several beneficial effects. First, it reduces the adhesion of the compositions to the inner surface of the mouth, thereby increasing the patient's ability to swallow the compositions. Second, the film may aid in masking the unpleasant taste of certain drugs. Third, the film coating may protect the compositions of the present invention from atmospheric degradation. Polymeric films that may be used in preparing the swallowable compositions of the present invention include vinyl polymers such as polyvinylpyrrolidone, polyvinyl alcohol and acetate, cellulosics such as methyl and ethyl cellulose, hydroxyethyl cellulose and hydroxylpropyl methylcellulose, acrylates and methacrylates, copolymers such as the vinyl-maleic acid and styrene-maleic acid types, and natural gums and resins such as zein, gelatin, shellac and acacia. Pharmaceutical carriers and formulations for swallowable compounds are well known to those of ordinary skill in the art. See generally, e.g., WADE & WALLER, HANDBOOK OF PHARMACEUTICAL EXCIPIENTS ($2^{nd}$ ed. 1994).

In a specific embodiment of the present invention, the compositions may comprise chewable compositions. Chewable compositions are those that have a palatable taste and mouthfeel, are relatively soft and quickly break into smaller pieces and begin to dissolve after chewing such that they are swallowed substantially as a solution.

In order to create chewable compositions, certain ingredients should be included to achieve the attributes just described. For example, chewable compositions should include ingredients that create pleasant flavor and mouthfeel and promote relative softness and dissolvability in the mouth. The following discussion describes ingredients that may help to achieve these characteristics.

Chewable compositions preferably have a pleasant or palatable flavor. Palatable flavors may be achieved by including sweetening agents and/or flavorants. Sweetening agents that may be included in the compositions of the present invention include, by way of example and without limitation, sucrose, fructose, high fructose corn syrup, dextrose, saccharin sodium, maltodextrin, aspartame, potassium acesulfame, neohesperidin dihydrochalcone, sucralose, monoammonium glycyrrhizinate, and others known to those of ordinary skill in the art. As used herein, the term "flavorant" means natural or artificial compounds used to impart a pleasant flavor and often odor to a pharmaceutical preparation. Flavorants that may be used in the present invention include, for example and without limitation, natural and synthetic flavor oils, flavoring aromatics, extracts from plants, leaves, flowers, and fruits and combinations thereof. Such flavorants include, by way of example and without limitation, anise oil, cinnamon oil, vanilla, vanillin, cocoa, chocolate, natural chocolate flavor, menthol, grape, peppermint oil, oil of wintergreen, clove oil, bay oil, anise oil, eucalyptus, thyme oil, cedar leave oil, oil of nutmeg, oil of sage, oil of bitter almonds, cassia oil; citrus oils, such as lemon, orange, lime and grapefruit oils; and fruit essences, including apple, pear, peach, berry, wildberry, date, blueberry, kiwi, strawberry, raspberry, cherry, plum, pineapple, and apricot. All of these flavorants are commercially available. In a specific embodiment of the present invention, flavorants that may be used include natural berry extracts and natural mixed berry flavor, as well as citric and malic acid. The amount of flavorants used may depend on a number of factors, including desired taste characteristics. While not necessary, one or more of these sweetening agents and/or flavorants also may be included in the swallowable compositions of the present invention.

In addition to having a palatable flavor, chewable compositions also should have a pleasant mouthfeel. A variety of ingredients can be included in the compositions of the present invention to enhance mouthfeel.

In the chewable compositions of the present invention, sugars such as white sugar, corn syrup, sorbitol (solution), maltitol (syrup), oligosaccharide, isomaltooligosaccharide, sucrose, fructose, lactose, glucose, lycasin, xylitol, lactitol, erythritol, mannitol, isomaltose, dextrose, polydextrose, dextrin, compressible cellulose, compressible honey, compressible molasses and mixtures thereof may be added to improve mouthfeel and palatability. Further, by way of example and without limitation, fondant or gums such as gelatin, agar, arabic gum, guar gum, and carrageenan may be added to improve the chewiness of the compositions. Fatty materials that may be included in the present invention include, by way of example and without limitation, vegetable oils (including palm oil, palm hydrogenated oil, corn germ hydrogenated oil, castor hydrogenated oil, cotton-seed oil, olive oil, peanut oil, palm olein oil, and palm stearin oil), animal oils (including refined oil and refined lard whose melting point ranges from 30° to 42° C.), Cacao fat, margarine, butter, and shortening.

Alkyl polysiloxanes (commercially available polymers sold in a variety of molecular weight ranges and with a variety of different substitution patterns) also may be used in the present invention to enhance the texture, the mouthfeel, or both of the chewable nutritional supplement compositions described herein. By "enhance the texture" it is meant that the alkyl polysiloxane improves one or more of the stiffness, the brittleness, and the chewiness of the chewable supplement, relative to the same preparation lacking the alkyl polysiloxane. By "enhance the mouthfeel" it is meant that the alkyl polysiloxane reduces the gritty texture of the supplement once it has liquefied in the mouth, relative to the same preparation lacking the alkyl polysiloxane.

Alkyl polysiloxanes generally comprise a silicon and oxygen-containing polymeric backbone with one or more alkyl groups pending from the silicon atoms of the back bone. Depending upon their grade, they can further comprise silica gel. Alkyl polysiloxanes are generally viscous oils. Exemplary alkyl polysiloxanes that can be used in the swallowable, chewable or dissolvable compositions of the present invention include, by way of example and without limitation, monoalkyl or dialkyl polysiloxanes, wherein the alkyl group is independently selected at each occurrence from a $C_1$-$C_6$-alkyl group optionally substituted with a phenyl group. A specific alkyl polysiloxane that may be used is dimethyl polysiloxane (generally referred to as simethicone). More specifically, a granular simethicone preparation designated simethicone GS may be used. Simethicone GS is a preparation which contains 30% simethicone USP. Simethicone USP contains not less than about 90.5% by weight $(CH_3)_3$—$Si\{OSi(CH_3)_2\}CH_3$ in admixture with about 4.0% to about 7.0% by weight $SiO_2$.

To prevent the stickiness that can appear in conventional chewable compositions and to facilitate conversion of the active ingredients to emulsion or suspension upon taking, the compositions of the present invention, may further comprise emulsifiers such as, by way of example and without limitation, glycerin fatty acid ester, sorbitan monostearate, sucrose fatty acid ester, lecithin and mixtures thereof. In a specific embodiment, one or more of such emulsifiers may be present in an amount of about 0.01% to about 5.0%, by weight of the administered compositions. If the level of emulsifier is lower or higher than the said range, the emulsification cannot be realized, or wax value will rise.

Chewable compositions should begin to break and dissolve in the mouth shortly after chewing begins such that the compositions can be swallowed substantially as a solution. The dissolution profile of chewable compositions may be enhanced by including rapidly water-soluble fillers and excipients. Rapidly water-soluble fillers and excipients preferably dissolve within about 60 seconds of being wetted with saliva. Indeed, it is contemplated that if enough water-soluble excipients are included in the compositions of the present invention, they may become dissolvable rather than chewable composition forms. Examples of rapidly water soluble fillers suitable for use with the present invention include, by way of example and without limitation, saccharides, amino acids and the like. In a specific embodiment, the saccharide may be a mono-, di- or oligosaccharide. Examples of saccharides which may be added to the compositions of the present invention include, by way of example and without limitation, sorbitol, glucose, dextrose, fructose, maltose and xylitol (all monosaccharides); and sucrose, lactose, glucose, galactose and mannitol (all disaccharides). Other suitable saccharides are oligosaccharides. Examples of oligosaccharides are dextrates and maltodextrins. Other water soluble excipients that may be used with the present invention include, by way of example and without limitation, amino acids such as alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine and valine.

Disintegrants also may be included in the compositions of the present invention in order to facilitate dissolution. Disentegrants, including permeabilising and wicking agents, are capable of drawing water or saliva up into the compositions which promotes dissolution from the inside as well as the outside of the compositions. Such disintegrants, permeabilising and/or wicking agents that may be used in the present invention include, by way of example and without limitation, starches, such as corn starch, potato starch, pre-gelatinized and modified starches thereof, cellulosic agents, such as Ac-di-sol, montmorrilonite clays, cross-linked PVP, sweeteners, bentonite, microcrystalline cellulose, croscarmellose sodium, alginates, sodium starch glycolate, gums, such as agar, guar, locust bean, karaya, pectin, Arabic, xanthan and tragacanth, silica with a high affinity for aqueous solvents, such as colloidal silica, precipitated silica, maltodextrins, beta-cyclodextrins, polymers, such as carbopol, and cellulosic agents, such as hydroxymethylcellulose, hydroxypropylcellulose and hydroxyopropylmethylcellulose.

Finally, dissolution of the compositions may be facilitated by including relatively small particles sizes of the ingredients used.

In addition to those described above, any appropriate fillers and excipients may be utilized in preparing the swallowable, chewable and/or dissolvable compositions of the present invention so long as they are consistent with the objectives described herein. For example, binders are substances used to cause adhesion of powder particles in granulations. Such compounds appropriate for use in the present invention include, by way of example and without limitation, acacia, compressible sugar, gelatin, sucrose and its derivatives, maltodextrin, cellulosic polymers, such as ethylcellulose, hydroxypropylcellulose, hydroxypropylmethyl cellulose, carboxymethylcellulose sodium and methylcellulose, acrylic polymers, such as insoluble acrylate ammoniomethacrylate copolymer, polyacrylate or polymethacrylic copolymer, povidones, copovidones, polyvinylalcohols, alginic acid, sodium alginate, starch, pregelatinized starch, guar gum, polyethylene glycol and others known to those of ordinary skill in the art.

Diluents also may be included in the compositions of the present invention in order to enhance the granulation of the compositions. Diluents can include, by way of example and without limitation, microcrystalline cellulose, sucrose, dicalcium phosphate, starches, lactose and polyols of less than 13 carbon atoms, such as mannitol, xylitol, sorbitol, maltitol and pharmaceutically acceptable amino acids, such as glycin, and their mixtures.

Lubricants are substances used in composition formulations that reduce friction during composition compression.

Lubricants that may be used in the present invention include, by way of example and without limitation, stearic acid, calcium stearate, magnesium stearate, zinc stearate, talc, mineral and vegetable oils, benzoic acid, poly(ethylene glycol), glyceryl behenate, stearyl fumarate, and others known to those of ordinary skill in the art.

Glidants improve the flow of powder blends during manufacturing and minimize composition weight variation. Glidants that may be used in the present invention include, by way of example and without limitation, silicon dioxide, colloidal or fumed silica, magnesium stearate, calcium stearate, stearic acid, cornstarch, talc and others known to those of ordinary skill in the art.

Colorants also may be included in the nutritional supplement compositions of the present invention. As used herein, the term "colorant" includes compounds used to impart color to pharmaceutical preparations. Such compounds include, by way of example and without limitation, FD&C Red No. 3, FD&C Red No. 20, FD&C Yellow No. 6, FD&C Blue No. 2, D&C Green No. 5, FD&C Orange No. 5, D&C Red No. 8, caramel, and ferric oxide, red and others known to those of ordinary skill in the art. Coloring agents also can include pigments, dyes, tints, titanium dioxide, natural coloring agents, such as grape skin extract, beet red powder, beta carotene, annato, carmine, turmeric, paprika and others known to those of ordinary skill in the art. It is recognized that no colorant is required in the nutritional supplement compositions described herein.

If desired, the compositions of the present invention may be sugar coated or enteric coated by standard techniques. The unit dose forms may be individually wrapped, packaged as multiple units on paper strips or in vials of any size, without limitation. The swallowable, chewable or dissolvable compositions of the present invention may be packaged in unit dose, rolls, bulk bottles, blister packs and combinations thereof, without limitation.

The swallowable, chewable or dissolvable compositions of the present invention may be prepared using conventional methods and materials known in the pharmaceutical art. For example, U.S. Pat. Nos. 5,215,754 and 4,374,082 relate to methods for preparing swallowable compositions. U.S. Pat. No. 6,495,177 relates to methods to prepare chewable nutritional supplements with improved mouthfeel. U.S. Pat. No. 5,965,162, relates to compositions and methods for preparing multi-vitamin comestible units which disintegrate quickly in the mouth, especially when chewed. Further, all pharmaceutical carriers and formulations described herein are well known to those of ordinary skill in the art, and determination of workable proportions in any particular instance will generally be within the capability of the person skilled in the art. Details concerning any of the excipients of the invention may be found in WADE & WALLER, HANDBOOK OF PHARMACEUTICAL EXCIPIENTS (2nd ed. 1994). All active ingredients, fillers and excipients are commercially available from companies such as Aldrich Chemical Co., FMC Corp, Bayer, BASF, Alexi Fres, Witco, Mallinckrodt, Rhodia, ISP, and others.

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description. The invention will be further illustrated by the following non-limiting examples.

EXAMPLES

Without further elaboration, it is believed that one skilled in the art, using the preceding description, can utilize the present invention to the fullest extent. The following examples are illustrative only, and not limiting of the remainder of the disclosure in any way whatsoever.

Example 1

A composition of the following formulation was prepared in chewable form:

| | |
|---|---|
| Vitamin A (acetate) | 1100 IU |
| Beta Carotene | 600 IU |
| Vitamin $B_1$ (thiamine mononitrate) | 1.6 mg |
| Vitamin $B_2$ (riboflavin) | 1.8 mg |
| Vitamin $B_3$ (niacinamide) | 15 mg |
| Vitamin $B_6$ (pyridoxine hydrochloride) | 2.5 mg |
| Vitamin $B_9$ (folic acid) | 1000 µg |
| Vitamin $B_{12}$ (cyanocobalamin) | 5 µg |
| Vitamin C (ascorbic acid) | 60 mg |
| Vitamin D (cholecalciferol) | 400 IU |
| Vitamin E (d-alpha-tocopheryl acetate) | 30 IU |
| Iron (polysaccharide complex) | 29 mg |
| Magnesium (magnesium oxide) | 25 mg |
| Zinc (zinc oxide) | 15 mg |

Example 2

A study is undertaken to evaluate the effectiveness of the compositions of the present invention in the treatment of patients. The objective of the study is to determine whether oral intake of the compositions results in an improvement of the nutritional status of patients with regard to the specific vitamins and minerals contained in the administered compositions.

A double-blind, placebo controlled study is conducted over a six-month period. A total of 120 subjects (60 pregnant women entering the second trimester of pregnancy and 60 lactating women), aged 20-35 years, are chosen for the study. An initial assessment of the nutritional status of each woman is conducted. Vitamin A, beta carotene and vitamin $B_6$ are measured using high performance liquid chromatography. Erythrocyte transketolase activity is used to measure vitamin $B_1$ levels. Vitamin $B_2$ levels are determined by assessment of erythrocyte glutathione reductase activity. Vitamin $B_3$ levels are assessed by measuring urinary excretion of N'methylnicotinamide and its pyridone. Vitamin $B_9$ is measured by radioimmunoassay (RIA), specifically The Solid Phase No Biol Folic Acid Kit (Diagnostic Products, Los Angeles, Calif.). Vitamin $B_{12}$ is measured by RIA using human intrinsic factor as a binder. Vitamin C levels are measured by spectrophotometric and colorimetric methods. Vitamin D is measured using an extraction double-antibody RIA (Dia Sorin, Inc., Stillwater, Minn.). The peroxide hemolysis test is used to determine vitamin E status. Iron levels are measured using standard spectrophotometry. Similarly, magnesium levels are measured by absorbance of a magnesium chelate with xylidl blue at 660 nM. Zinc levels are assessed using flame atomic absorption spectrometry (Perkins Elmer 460, Norwalk, Conn.).

The 120 subjects are separated into four separate groups of 30 women. In a first group comprising only pregnant women and in a second group comprising only lactating women, each subject is administered one dosage form of the composition as described in Example 1 twice a day. In a third group comprising only pregnant women and in a fourth group comprising only lactating women, each subject is administered one placebo dosage form twice a day. Thus, dosage form administration occurs every 12 hours. No other nutritional supplements are taken by the subjects during the assessment period.

An assessment of the nutritional status of each woman is conducted utilizing the methods described above at one month intervals for a six month period. The data is evaluated using multiple linear regression analysis and a standard t-test. In each analysis, the baseline value of the outcome variable is included in the model as a covariant. Treatment by covariant interaction effects is tested by the method outlined by Weigel & Narvaez, 12 CONTROLLED CLINICAL TRIALS 378-94 (1991). If there are no significant interaction effects, the interaction terms are removed from the model. The regression model assumptions of normality and homogeneity of variance of residuals are evaluated by inspection of the plots of residuals versus predicted values. Detection of the temporal onset of effects is done sequentially by testing for the presence of significant treatment effects at 1, 2, 3, 4, 5, and 6 months, proceeding to the earlier time in sequence only when significant effects have been identified at each later time period. Changes from the baseline within each group are evaluated using paired t-tests. In addition, analysis of variance is performed on all baseline measurements and measurable subject characteristics to assess homogeneity between groups. All statistical procedures are conducted using the Statistical Analysis System (SAS Institute Inc., Cary, N.C.). An alpha level of 0.05 is used in all statistical tests.

A statistically significant improvement in the nutritional status of all vitamin and mineral levels measured is observed in the treated subjects over the controls upon completion of the study. Therefore, the study confirms that oral administration of the compositions of the present invention is effective in improving the nutritional status of patients.

While specific embodiments of the present invention have been described, other and further modifications and changes may be made without departing from the spirit of the invention. All further and other modifications and changes are included that come within the scope of the invention as set forth in the claims. The disclosure of all publications cited above are expressly incorporated by reference in their entireties to the same extent as if each were incorporated by reference individually.

What is claimed is:
1. A method comprising:
   administering a composition to a patient to supplement a nutritional deficiency in the patient, the composition comprising:
   about 880 IU to about 1320 IU vitamin A, about 480 IU to about 720 IU beta carotene, about 1.3 mg to about 1.9 mg vitamin B1, about 1.5 mg to about 2.2 mg vitamin B2, about 12 mg to about 18 mg vitamin B3, about 2 mg to about 3 mg vitamin B6, about 800 μg to about 1200 μg vitamin B9, about 4 μg to about 6 μg vitamin B12, about 48 mg to about 72 mg vitamin C, about 320 IU to about 480 IU vitamin D3, about 24 IU to about 36 IU vitamin E, about 23 mg to about 35 mg iron, about 20 mg to about 30 mg magnesium, about 12 mg to about 18 mg zinc; and
   one or more pharmaceutically-acceptable carriers;
   wherein said composition is substantially free of other added vitamins and minerals; and
   wherein the composition is administered in one or more tablets or capsules; or
   wherein the composition is sugar coated or enteric coated.

2. The method of claim 1, wherein said vitamin A is in the form of acetate.
3. The method of claim 1, wherein said vitamin B1 is in the form of thiamine mononitrate, wherein said vitamin B2 is in the form of riboflavin, wherein said vitamin B3 is in the form of niacinamide, wherein said vitamin B6 is in the form of pyridoxine hydrochloride, wherein said vitamin B9 is in the form of folic acid, and wherein said vitamin B12 is in the form of cyanocobalamin.
4. The method of claim 1, wherein said vitamin B3 comprises an equivalent molar amount of niacin.
5. The method of claim 1, wherein said vitamin B9 is in the form of folacin.
6. The method of claim 1, wherein said vitamin B9 is in the form of metafolin.
7. The method of claim 1, wherein said vitamin B9 is in the form of folate.
8. The method of claim 1, wherein said vitamin B9 comprises one or more natural isomers of folate consisting of (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof and 5-formimino-(6S)-tetrahydrofolic acid or a polyglutamyl derivative thereof.
9. The method of claim 1, wherein said vitamin C is in the form of ascorbic acid.
10. The method of claim 1, wherein said vitamin D3 is in the form of cholecalciferol.
11. The method of claim 1, wherein said vitamin E is in the form of d-alpha tocopheryl acetate.
12. The method of claim 1, wherein said vitamin E is in the form of d-alpha tocopheryl succinate.
13. The method of claim 1, wherein said iron is in the form of ferrous fumarate.
14. The method of claim 1, wherein said iron is in the form of polysaccharide iron complex.
15. The method of claim 1, wherein said magnesium is in the form of magnesium oxide.
16. The method of claim 1, wherein said zinc is in the form of zinc oxide.
17. The method of claim 1, wherein said one or more pharmaceutically acceptable carriers are selected from the group consisting of binders, diluents, lubricants, glidants, colorants, emulsifiers, disintegrants, starches, water, oils, alcohols, preservatives, sweetening agents, flavorants, and sugars.
18. The method of claim 17, wherein said sweetening agent is selected from one or more of the group consisting of sucrose, fructose, high fructose corn syrup, dextrose, saccharin sodium, maltodextrin, aspartame, potassium acesulfame, neohesperidin dihydrochalcone, sucralose, monoammonium glycyrrhizinate, and mixtures thereof.
19. The method of claim 17, wherein said flavorant is selected from one or more of the group consisting of a natural flavor oil, a synthetic flavor oil, a citrus oil, a fruit essence, an extract from a plant, an extract from a leaf, an extract from a flower, an extract from a fruit, a synthetic flavor, anise oil, cinnamon oil, peppermint oil, oil of wintergreen, clove oil, bay oil, anise oil, eucalyptus oil, thyme oil, cedar leave oil, oil of nutmeg, oil of sage, oil of bitter almonds, cassia oil, lemon oil, orange oil, lime oil, grapefruit oil, grape oil, apple essence, pear essence, peach essence, berry essence, wildberry essence, date essence, blueberry essence, kiwi essence, strawberry essence, raspberry essence, cherry essence, plum essence, pineapple essence, apricot essence, natural mixed berry flavor, citric acid, malic acid, vanilla, vanillin, cocoa, chocolate, menthol, and combinations thereof.

20. The method of claim 1, wherein said composition further comprises alkyl polysiloxane in an amount of about 0.05 weight percent to less than about one weight percent of the composition.

21. The method of claim 20, wherein said alkyl polysiloxane is in the form of dimethyl polysiloxane.

22. The method of claim 1, wherein said one or more pharmaceutically-acceptable carriers comprise fructose, stearic acid, natural mixed berry flavor, croscarmellose sodium, citric acid, magnesium stearate, silicon dioxide, and malic acid.

23. The method of claim 1, wherein said vitamins and minerals consist of: about 990 IU to about 1210 IU vitamin A; about 540 IU to about 660 IU beta carotene; about 1.5 mg to about 1.75 mg vitamin B1; about 1.6 mg to about 2 mg vitamin B2; about 13.5 mg to about 16.5 mg vitamin B3; about 2.3 mg to about 2.8 mg vitamin B6; about 900 μg to about 1100 μg vitamin B9; about 4.5 μg to about 5.5 μg vitamin B12; about 54 mg to about 66 mg vitamin C; about 360 IU to about 440 IU vitamin D3; about 27 IU to about 33 IU vitamin E; about 26 mg to about 32 mg iron; about 22.5 mg to about 27.5 mg magnesium; and about 13.5 mg to about 16.5 mg zinc.

24. The method of claim 1, wherein said vitamins and minerals consist of: about 1100 IU vitamin A; about 600 IU beta carotene; about 1.6 mg vitamin B1; about 1.8 mg vitamin B2; about 15 mg vitamin B3; about 2.5 mg vitamin B6; about 1000 μg vitamin B9; about 5 μg vitamin B12; about 60 mg vitamin C; about 400 IU vitamin D3; about 30 IU vitamin E; about 29 mg iron; about 25 mg magnesium; and about 15 mg zinc.

25. The method of claim 1, wherein said patient is pregnant.

26. The method of claim 1, wherein said patient is lactating.

27. The method of claim 1, wherein said nutritional deficiencies are a result of pregnancy.

28. The method of claim 1, wherein said nutritional deficiencies are a result of lactation.

29. The method of claim 1, wherein said nutritional deficiencies are a result of elevated metabolic demand.

30. The method of claim 1, wherein said nutritional deficiencies are a result of increased plasma volume.

31. The method of claim 1, wherein said nutritional deficiencies are a result of decreased concentrations of nutrient-binding proteins.

32. The method of claim 31, wherein said nutrient-binding proteins comprise one or more proteins selected from the group consisting of serum-ferritin, maltose-binding protein, lactoferrin, calmodulin, tocopheryl binding protein, riboflavin binding protein, retinal binding protein, transthyretin, high density lipoprotein-apolipoprotein A1, folic acid binding protein, and 25-hydroxyvitamin D binding protein.

33. The method of claim 1, wherein the one or more pharmaceutically-acceptable carriers are one or more selected from the group consisting of: binders, diluents, lubricants, glidants, colorants, emulsifiers, disintegrants;

wherein the binders are selected from the group consisting of: acacia, compressible sugar, gelatin, sucrose and its derivatives, maltodextrin, cellulosic polymers, ethylcellulose, hydroxypropylcellulose, hydroxypropylmethyl cellulose, carboxymethylcellulose sodium, methylcellulose, acrylic polymers, insoluble acrylate ammoniomethacrylate copolymer, polyacrylate or polymethacrylic copolymer, povidones, copovidones, polyvinylalcohols, alginic acid, sodium alginate, starch, pregelatinized starch, guar gum, and polyethylene glycol;

wherein the diluents are selected from the group consisting of: microcrystalline cellulose, sucrose, dicalcium phosphate, starches, lactose and polyols of less than 13 carbon atoms, such as mannitol, xylitol, sorbitol, maltitol and pharmaceutically acceptable amino acids, such as glycine, and their mixtures;

wherein the lubricants are selected from the group consisting of: stearic acid, calcium stearate, magnesium stearate, zinc stearate, talc, mineral and vegetable oils, benzoic acid, poly(ethylene glycol), glyceryl behenate, and stearyl fumarate; and wherein the glidants are selected from the group consisting of: silicon dioxide, colloidal or fumed silica, magnesium stearate, calcium stearate, stearic acid, cornstarch, and talc; and wherein the emulsifiers are selected from the group consisting of: glycerin fatty acid ester, sorbitan monostearate, sucrose fatty acid ester, lecithin and mixtures thereof; and wherein the disintegrants are selected from the group consisting of: starches, such as corn starch, potato starch, pre-gelatinized and modified starches thereof, cellulosic agents, Ac-di-sol, montmorrilonite clays, cross-linked PVP, sweeteners, bentonite, microcrystalline cellulose, croscarmellose sodium, alginates, sodium starch glycolate, gums, agar, guar, locust bean, karaya, pectin, Arabic, xanthan and tragacanth, silica with a high affinity for aqueous solvents, colloidal silica, precipitated silica, maltodextrins, beta-cyclodextrins, polymers, carbopol, cellulosic agents, hydroxymethylcellulose, hydroxypropylcellulose and hydroxyopropylmethylcellulose.

34. The method of claim 1, wherein the composition is provided in one or a plurality of unit dose form(s) and wherein the unit dose form(s) is individually wrapped, packaged as multiple units on paper strips, packaged in a vial, packaged in blister packs, and packaged in bottles.

* * * * *